US012458344B2

(12) United States Patent
Spenciner et al.

(10) Patent No.: US 12,458,344 B2
(45) Date of Patent: Nov. 4, 2025

(54) SUTURE HAVING ADAPTABLE SURFACE CHARACTERISTICS, AND RELATED SYSTEMS AND METHODS

(71) Applicant: Medos International Sarl, Le Locle (CH)

(72) Inventors: David B. Spenciner, North Attleboro, MA (US); Dennis Connelly, Arlington, MA (US); Gregory R. Whittaker, Stoneham, MA (US)

(73) Assignee: Medos International Sarl, Le Locle (CH)

( * ) Notice: Subject to any disclaimer, the term of this patent is extended or adjusted under 35 U.S.C. 154(b) by 362 days.

(21) Appl. No.: 17/814,736

(22) Filed: Jul. 25, 2022

(65) Prior Publication Data

US 2023/0030543 A1 Feb. 2, 2023

Related U.S. Application Data

(60) Provisional application No. 63/225,664, filed on Jul. 26, 2021.

(51) Int. Cl.
*A61B 17/06* (2006.01)

(52) U.S. Cl.
CPC .................. *A61B 17/06166* (2013.01); *A61B 2017/06176* (2013.01); *A61B 2017/0618* (2013.01)

(58) Field of Classification Search
None
See application file for complete search history.

(56) References Cited

U.S. PATENT DOCUMENTS

| | | | |
|---|---|---|---|
| 3,123,077 | A | 3/1964 | Alcamo |
| 3,125,615 | A | 3/1964 | Redner |
| 4,018,085 | A | 4/1977 | Alley et al. |
| 4,094,637 | A | 6/1978 | Feess et al. |
| 6,142,968 | A | 11/2000 | Pigg et al. |
| 6,778,236 | B1 | 8/2004 | Crawford et al. |
| 7,544,627 | B2 | 6/2009 | Tao et al. |
| 8,251,968 | B2 | 8/2012 | Fernfors |
| 8,343,411 | B2 | 1/2013 | Arora et al. |
| 8,777,988 | B2 | 7/2014 | Leung et al. |
| 8,793,863 | B2 | 8/2014 | Hunter et al. |
| 8,828,053 | B2 | 9/2014 | Sengun et al. |

(Continued)

FOREIGN PATENT DOCUMENTS

| | | | |
|---|---|---|---|
| BE | 1014364 | A6 | 9/2003 |
| EP | 3072474 | A2 | 9/2016 |

(Continued)

*Primary Examiner* — Shaun L David
(74) *Attorney, Agent, or Firm* — BakerHostetler

(57) ABSTRACT

A suture construct that is elongate along a longitudinal direction and configured to change in size from a first configuration to a second configuration includes an outer layer of material that extends along the longitudinal direction and has a plurality of intertwined fibers that comprise a first sub-set of fibers crossed by a second sub-set of fibers at respective intersections, such that the first subset of fibers and the second subset of fibers are configured to reorient relative to each other in a manner causing the outer layer of material to change in one or more of surface texture and visual appearance as the suture construct changes between the first and second configurations.

11 Claims, 6 Drawing Sheets

(56) References Cited

U.S. PATENT DOCUMENTS

| | | | | |
|---|---|---|---|---|
| 8,870,915 | B2 | 10/2014 | Mayer et al. | |
| 8,975,210 | B2 | 3/2015 | Arora et al. | |
| 9,125,727 | B2 | 9/2015 | Dallafior | |
| 9,157,188 | B2 | 10/2015 | Prodoehl | |
| 9,173,645 | B2 | 11/2015 | Overes et al. | |
| 9,427,430 | B2 | 8/2016 | Stokes et al. | |
| 9,597,064 | B2 | 3/2017 | Overes et al. | |
| 9,724,080 | B2 | 8/2017 | Corrao et al. | |
| 9,743,919 | B2 | 8/2017 | Manos et al. | |
| 2005/0004601 | A1* | 1/2005 | Kong | A61B 90/92 606/228 |
| 2006/0178701 | A1* | 8/2006 | Schmieding | D04C 1/06 606/228 |
| 2008/0064839 | A1* | 3/2008 | Hadba | A61L 17/10 606/228 |
| 2008/0082113 | A1* | 4/2008 | Bishop | A61L 17/145 606/232 |
| 2008/0103528 | A1* | 5/2008 | Zirps | A61B 90/94 606/228 |
| 2008/0281355 | A1 | 11/2008 | Mayer et al. | |
| 2009/0248071 | A1* | 10/2009 | Saint | A61B 17/06066 606/232 |
| 2009/0275963 | A1* | 11/2009 | May | A61L 17/10 606/228 |
| 2011/0264138 | A1* | 10/2011 | Avelar | A61B 90/94 606/228 |
| 2011/0319932 | A1* | 12/2011 | Avelar | A61B 90/90 606/228 |
| 2013/0172931 | A1* | 7/2013 | Gross | A61B 17/06166 606/228 |
| 2014/0257378 | A1* | 9/2014 | Norton | A61B 17/06166 606/228 |
| 2015/0173753 | A1* | 6/2015 | Spivey | A61B 17/06166 606/228 |
| 2016/0256252 | A1 | 9/2016 | Sim | |
| 2017/0059890 | A1 | 3/2017 | Wilson | |
| 2017/0224338 | A1 | 8/2017 | Sung | |
| 2018/0221022 | A1 | 8/2018 | Choe et al. | |
| 2019/0380708 | A1* | 12/2019 | Allen | D04C 3/30 |
| 2020/0129172 | A1* | 4/2020 | Dumanian | A61B 17/8869 |
| 2020/0178951 | A1 | 6/2020 | Johnson et al. | |
| 2021/0137520 | A1* | 5/2021 | Asfora | A61B 17/06066 |
| 2022/0167964 | A1* | 6/2022 | Meglan | A61B 90/37 |
| 2022/0184270 | A1* | 6/2022 | Diaz-Chiosa | A61L 17/105 |
| 2022/0395273 | A1* | 12/2022 | Perkins | A61B 17/1146 |
| 2023/0079284 | A1* | 3/2023 | Siccardi | A61B 90/92 606/228 |

FOREIGN PATENT DOCUMENTS

| | | | |
|---|---|---|---|
| EP | 3202336 | A1 | 8/2017 |
| JP | 51-064086 | A | 6/1976 |
| KR | 10-2019-0030062 | A | 3/2019 |
| RU | 2619728 | C2 | 5/2017 |

* cited by examiner

SUTURE HAVING ADAPTABLE SURFACE CHARACTERISTICS, AND RELATED SYSTEMS AND METHODS

CROSS REFERENCE TO RELATED APPLICATIONS

This application claims benefit under 35 U.S.C. § 119(e) of Provisional U.S. Patent Application No. 63/225,664, filed Jul. 26, 2021, the entire contents of which are hereby incorporated by reference herein.

TECHNICAL FIELD

The present invention relates to suture materials, and more particularly to suture materials that are configured to undergo a change in surface texture and/or surface visual presentation responsive to implantation.

BACKGROUND

Injuries to tissue such as cartilage, skin, muscle, bone, tendon and ligament, frequently require surgical intervention to repair the damage and facilitate healing. Surgical procedures to repair tissue damage are often performed using sutures connected to one or more anchoring device implanted in or adjacent to the damaged tissue. The sutures can also be passed through or around the tissue according to a variety of surgical techniques to secure the repair. The sutures can also interconnect two or more anchors used to perform the repair. Suture anchors have been fabricated with bodies formed from a variety of materials including nonabsorbable materials such as metals and durable polymers, as well as bioabsorbable materials such as absorbable polymers, bioceramics, absorbable composites and processed bone.

Suture anchors, for example, display advantages in relation to fixation within bone material because the relatively soft and pliable nature of textile suture material allows suture anchors to generally fit within smaller pre-drilled holes in bone relative to other types of bone anchors, thus reducing the amount of bone that must be removed prior to anchor insertion. Moreover, sutures can be connected through or around suture anchors in a fixed or a sliding manner, for example, using eyelets or other passages in an anchor body, and can be secured using stationary or sliding knots, interference among anchor components, interference between an anchor and surrounding tissue, or other means. Some suture anchors are designed for suture to slide unidirectional through or around the anchor, enabling a surgical repair to be tightened by tensioning a portion of the suture with respect to the anchor.

Among their many surgical applications, suture anchors are used with sutures to re-attach damaged tendons or ligaments to bone, to tighten compromised tissue surrounding articulating joints, and to repair tears in cartilage, such as torn meniscal cartilage in a knee. In some applications, two or more anchors joined by an adjustable length of suture enable a tissue tear to be cinched closed, or compromised tissue to be stabilized.

Of great importance in suture anchor design is maximizing retention strength (such as the retention strength of the anchor in bone) to minimize the risk of anchor breakage or pullout (such as from bone) when an attached suture is tensioned with respect to the anchor. Some drawbacks of suture anchors can include, depending on the relevant circumstances: a fixation strength that can be lower than other anchor types due to the difficulty in setting some types of suture anchors; and achieving expansion of suture anchors in hard bone material, such as cortical bone. Other issues observed with suture anchors include laxity (i.e., loosening) and creep over time, as well as long term micro-motion at the anchor-anatomy interface. These issues can decrease the amount of compression applied to a repair. Additionally, over time a gap can be introduced into the repair which is not optimal for healing.

SUMMARY

According to an embodiment of the present disclosure, a suture construct that is elongate along a longitudinal direction and configured to change in size from a first configuration to a second configuration includes a layer of material that defines an outer surface of the suture construct and extends along the longitudinal direction and around a central axis oriented along the longitudinal direction. The layer of material includes a plurality of fibers and a plurality of barbs extending within the plurality of fibers. Outer ends of the barbs reside longitudinally between the fibers when the suture construct is in the first configuration. The barbs are deployable such that the outer ends of the barbs extend outward from the outer surface along a radial direction perpendicular to the central axis when the suture construct is in the second configuration.

According to another embodiment of the present disclosure, a suture construct that is elongate along a longitudinal direction and configured to change in size from a first configuration to a second configuration includes an outer layer of material that extends along the longitudinal direction and has a plurality of intertwined fibers that comprise a first sub-set of fibers crossed by a second sub-set of fibers at respective intersections. Fibers of at least one of the first sub-set of fibers and the second sub-set of fibers have discrete visual indicia. The outer layer of material is configured such that the discrete visual indicia have a first visualization characteristic when the suture construct is in the first configuration and a second visualization characteristic when the suture construct is in the second configuration, such that the second visualization characteristic is visually different than the first visualization characteristic.

According to an additional embodiment of the present disclosure, a suture construct that is elongate along a longitudinal direction and configured to change in size from a first configuration to a second configuration includes an outer layer of material that extends along the longitudinal direction and has a plurality of intertwined fibers that comprise a first sub-set of fibers crossed by a second sub-set of fibers at respective intersections, such that the first subset of fibers and the second subset of fibers are configured to reorient relative to each other in a manner causing the outer layer of material to change in one or more of surface texture and visual appearance as the suture construct changes between the first and second configurations.

In further embodiments of the present disclosure, methods of repairing an anatomical structure include deploying any of the sutures and/or suture materials described herein.

BRIEF DESCRIPTION OF THE DRAWINGS

The foregoing summary, as well as the following detailed description of illustrative embodiments of the present application, will be better understood when read in conjunction with the appended drawings. For the purposes of illustrating the features of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

Figure 1A:
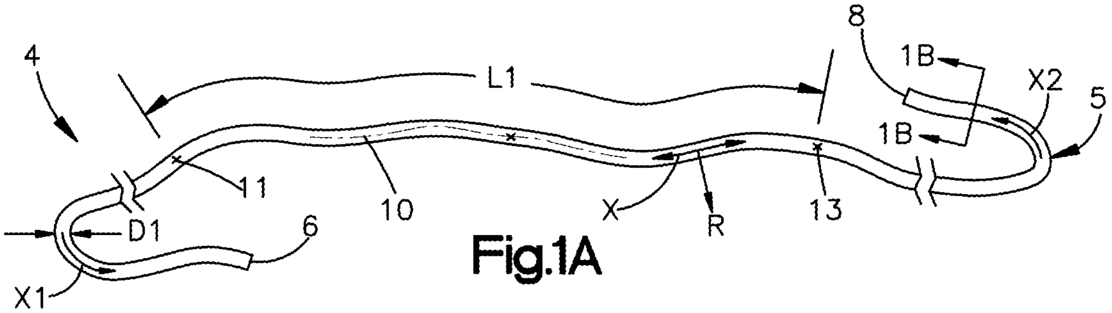
FIG. 1A is a perspective view of a suture, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately", "about", and "substantially", as used herein with respect to dimensions, angles, ratios, and other geometries, takes into account manufacturing tolerances. Further, the terms "approximately", "about", and "substantially" can include 10% greater than or less than the stated dimension, ratio, or angle. Further, the terms "approximately", "about", and "substantially" can equally apply to the specific value stated.

The term "suture construct", as used herein, refers to a constructed body of constituent suture material(s) that are combined or otherwise aggregated together to form the body. By way of non-limiting examples, the term "suture construct", as used herein, encompasses sutures, fabrics, tapes, flat-braids, sleeves, tubes, jackets, meshes, anchors, knots, and the like, including various combinations of the foregoing suture constructs.

The term "fiber", as used herein, refers to a discrete, elongated body that is a constituent material capable of being braided, knit, woven, wound, intertwined, or otherwise aggregated with one or more other bodies of constituent material to make a suture construct. It should be appreciated that the term "fiber", as used herein, encompasses a discrete, elongated body of constituent material that is itself constructed of one or more smaller bodies of constituent material. For example, the term "fiber", as used herein, encompasses both monolithic and polylithic structures, and can be a monofilament- or multifilament-type fiber.

The term filament, as used herein, refers to an elongated monolithic body, which can be employed as a constituent material within a fiber and/or a suture construct. Thus, in the following disclosure, a filament can be referenced as a constituent component of a fiber, but a fiber will not be referenced as a constituent component of a filament.

The terms "crosses" and "picks", as used herein, each refer to one fiber that crosses or otherwise intersects another fiber within a suture construct.

The term "pick-count", as used herein, refers to the quantity of fibers (picks) along one (1) inch of suture length. Pick-count is typically defined as "picks per inch" (PPI), or "picks per centimeter" (PPC).

The embodiments disclosed herein pertain to suture constructs, particularly laxity-reducing suture constructs, having constructions that are insertable within or adjacent an anatomical structure in a first configuration and thereafter automatically physically transform into a second configuration responsive to exposure to an aqueous environment (i.e., hydration), such as the in vivo environment at the implantation/repair site. The automatic physical transformation can provide significant advantages for treatment and healing.

In some of the embodiments described below, the automatic physical transformation changes a surface texture of the suture construct, thereby increasing its retention and/or fixation strength. The change in surface texture can involve deployment of retention members, such as barbs, that can grip tissue at the suture-tissue interface or otherwise limit relative translation, such as suture slide and/or micro-motion at the suture-tissue interface, thus creating a more stable healing environment. Additionally, the automatic physical transformation can occur over such a duration that the implantation procedure can be complete before the physical transformation begins in earnest. In this manner, the suture construct can be inserted through and/or along soft tissue as needed while in a neutral configuration before the surface texture changes to a grip-increasing configuration.

In additional embodiments described below, the physical transformation changes a visual presentation of an outer surface of the suture construct. This change in visual presentation provides visually observable information or "feedback" pertaining to a physical condition (e.g., deformation or "strain") of the suture construct. By way of a non-limiting example, such change involves changing the orientation and/or relative position of visual indicia carried by at least some of the fibers relative to other fibers in the suture construct, resulting in an optically perceivable change in visual presentation between the first and second configurations. Such physical transformation can alert a physician if such a change in the suture's physical condition occurs during or after surgery, thereby allowing the physician to assess whether intra-operative adjustments are necessary and/or whether additional intra- or post-operative treatments would enhance treatment.

These benefits are derived in large part from the inventors' surprising and unexpected discovery that when a laxity-reducing suture construct (such as DYNACORD™, available from DePuy Synthes Mitek Sports Medicine of Raynham, Massachusetts, United States of America) undergoes a reduction in length responsive to hydration, the intersection angles at which the braided fibers cross one another increase, thereby increasing the average pick-count of the suture construct. Thus, the braid angle (the angle at which the fibers are oriented relative to the longitudinal axis of the suture construct) also increases as the suture construct reduces in length. The embodiments of the present disclosure employ this phenomenon advantageously to actuate additional transformative changes in the suture construct(s), such as the changes in surface texture and visual presentation mentioned above, and described in more detail below.

Referring to FIG. 1A, a laxity-reducing suture construct according to an example of the present disclosure can be a suture 4 having a flexible, substantially cylindrical body 5 that extends from a first end 6 to a second end 8 along a central, longitudinal axis 10. The suture 4 extends along a longitudinal direction X oriented along the longitudinal axis 10. It should be appreciated that the longitudinal direction X, as referred to herein, is bi-directional and has two (2) mono-directional components, specifically a first longitudinal direction X1 that extends from the second end 8 to the first end 6, and a second longitudinal direction X2 that extends from the first end 6 to the second end 8. Thus, the first and second longitudinal directions X1, X2 are opposite each other. The suture 4, or any portion thereof, defines a longitudinal dimension, such as a length L1, measured along the longitudinal axis 10 (and thus also along the longitudinal direction X). Although FIG. 1A shows the length L1 as being measured between two (2) intermediate reference locations 11, 13 along the longitudinal axis 10, for purposes of the following disclosure the length L1 can be measured along any respective longitudinal portion of the suture 4, including from the first end 6 to the second end 8, for example. The suture 4, or any portion thereof, also defines a cross-sectional dimension D1, measured along a radial direction R that is perpendicular to the longitudinal direction X. It should be appreciated that, as used herein, the terms "longitudinal", "longitudinally", and derivatives thereof refer to the longitudinal direction X, and the terms "radial", "radially", and derivatives thereof refer to the radial direction R. It should be appreciated that, because the cross-sectional dimension(s) D1 of the suture 4 are nominal in relation to the length L1, the suture 4 can be referred to as a "one-dimensional" suture construct.

The suture 4 is configured to undergo a physical transformation responsive to hydration, such as experienced when the suture 4 is located in vivo during and after implantation. This physical transformation includes a change in size for the suture 4 from a first configuration to a second configuration responsive to hydration. It should be appreciated that this size transformation is independent of any physical manipulation, repositioning, or reorientation performed by a physician. For example, when hydrated, the suture 4 can be configured to swell along the radial direction R, thus increasing the cross-sectional dimension D1, and to contract along the longitudinal direction X, thus decreasing the length L1.

Figure 1B:
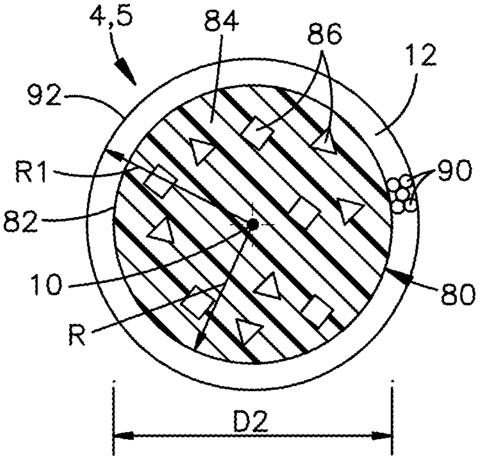
FIG. 1B is a sectional end view of the suture taken along section line 1B-1B of FIG. 1A.

Referring now to FIG. 1B, the suture 4 includes at least one transformative material, such as a core structure 80, the actuates the physical transformation (i.e., change in size) of the suture 4. The core structure 80 can have a circular cross-sectional shape. The suture 4 can also have a circular cross-sectional shape, although other cross-sectional shapes for the suture 4 and/or the core 80 are within the scope of the present disclosure. In the present embodiment, the longitudinal axis 10 of the suture is preferably centrally located with respect to the core structure 80. Thus, the longitudinal axis 10 of the suture 4 can also characterized as the central axis 10 of the core structure 80. Thus, the core structure 80 can be referred to as an "axial core" 80 (or simply a "core" 80). In other embodiments, the core structure 80 can be eccentrically located within the suture 4 (i.e., a central axis of the core 80 can be offset from the longitudinal axis 10 of the suture 4).

The core 80 defines a cross-sectional dimension D2 measured between opposite locations of an outer surface 82 of the core 80 along the radial direction R. In the illustrated embodiment in which the core 80 has a circular cross-sectional shape, the cross-sectional dimension D2 is the outer diameter of the core 80. When in a neutral or non-swollen configuration, the cross-sectional dimension D2 is preferably in a range from about 0.004 inch (about 0.102 mm) to about 0.040 inch (about 1.016 mm). Additionally, the core 80 (regardless of shape) has a durometer (i.e., hardness) preferably in a range from about 20 A to about 90 A. In the present embodiment, the core 80 is configured to transition from the first configuration to the second configuration by swelling along the radial direction R, thus increasing the cross-sectional dimension D2, when hydrated. This swelling action also preferably causes the core 80 to contract axially (i.e., along the longitudinal direction X), thus reducing the length L1 of the suture 4 as it transitions to the second configuration.

Figure 1C:
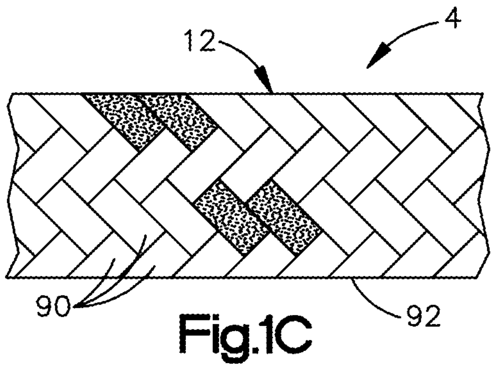
FIG. 1C is a side view of a portion of the suture illustrated in FIG. 1A.

The suture 4 can include a layer of material 12 that extends around a circumference of the outer surface 82 of the core 80. Thus, the layer of material 12 can be referred to as an "outer" layer of material" 12. The layer of material 12 also extends along the longitudinal direction X, such as along an entire length L1 of the suture 4 from the proximal end 6 to the distal end 8. The layer of material 12 can also be referred to as a "sleeve", "jacket", or "sheath" of the suture 4. As shown in FIGS. 1B and 1C, the jacket 12 is constructed of a plurality of fibers 90 that are braided, knit, woven, wound, or otherwise intertwined together such that at least some of the fibers 90 in the jacket 12 are crossed by other fibers 90 in the jacket 12. In this manner, each crossed fiber 90 has a pick-count, as defined above. The jacket 12 also has a pick-count. The jacket 12 defines an outer surface 92, which in the present embodiment defines an outer surface of the suture 4. As shown in FIG. 1B, the outer surface 92 is spaced from the longitudinal axis 10 at a radial distance R1 measured along the radial direction R. As the core 80 swells radially and contracts longitudinally, it forces the jacket 12 to expand radially, thus increasing dimension D1, and to contract longitudinally, thus decreasing the suture length L1. The swelling of the core 80 also causes the fibers 90 in the jacket 12 to reposition and reorient relative to each other, as described in more detail below. The fibers 90 can have a material composition selected from a group of materials that includes polyethylene terephthalate (PET), ultra-high-molecular-weight polyethylene (UHMWPE), polydioxanone (PDS), polypropylene (PP), nylon, and stainless steel, for example, and can be monofilament or multifilament fibers, and can be employed with or without colorants, as desired. It should be appreciated that in additional embodiments, the suture 4 can include one or more additional or "inner" layers of material extending annularly between the core 80 and the outer layer of material 12. Such inner layer(s) of material can be constructed of one or more additional pluralities of fibers 90 that are braided, knit, woven, wound, or otherwise intertwined together. The fibers 90 of the inner layer(s) can have material compositions selected from the aforementioned group of materials. Moreover, the fibers 90 of the inner layer(s) can have the same or different material compositions from those of the jacket 12.

To provide the swelling transformation described above, the core 80 preferably includes a highly-elastic polymeric thread 84 that is incorporated with one or more osmotically active substances 86 (i.e., substances that take up water), which causes the core 80 to swell. The polymeric thread 84 can be a filamentary polymer material (of a type which is non-degradable, partially degradable, or completely degradable). For instance, the polymeric thread 84 can be configured as a thermoplastic elastomer (polyurethane, polyester), a cross-linked elastomer (silicone, polyurethane, elastin, collagen) or a gel (polyethylene glycol, alginate, chitosan). The osmotically active substances 86 can include one or both of a salt (NaCl) and tri-calcium phosphate (TCP, which also advantageously facilitates boney ingrown within the core), although other osmotic materials can be employed, such as other biocompatible inorganic salts and aqueous solutions thereof, calcium chloride, calcium carbonate, or organic osmotically active molecules can be used, for example low-molecular-weight polysaccharides, such as dextran. In one example, the core 80 comprises a silicone thread incorporated with osmotically active substances that 86 include fine salt crystals and TCP. The amount of salt and TCP contained within the core 80 can be in a range of about 2 percent to about 40 percent by weight. It is to be appreciated that the polymer thread 84 can be extruded from a melt or from a solution, and the salt (NaCl) particles are preferably co-extruded or admixed to the polymer mass before extrusion. It is to be appreciated that the core 80 can be formed by other methods, such as molding, by way of non-limiting example.

It is to be appreciated that the osmotically active substances 86 can also or alternatively be embedded in a biocompatible gel or hydrogel (for example from the group of alginates, chitosans or copolymers thereof, polyacrylates, polyethylene glycol, etc.). An effect whose action is comparable in principle to the osmotically active substances can also be achieved by sole use of hydrogels. According to Fick's laws, particular importance is attached to the membrane surrounding the swelling system, which membrane critically influences the kinetics of osmosis by virtue of its permeation and diffusion properties for $H_2O$, and also by virtue of its thickness. The membrane can of course be made up of several layers or can also be provided with stable or soluble diffusion-inhibiting layers. If hydrogels are used, such a membrane-like property can also be achieved by means of a crosslinking density that increases considerably toward the outside. The concentration differences effecting osmosis are to be achieved between thread core and surrounding blood or interstitial and/or intrastitial fluid of the patient. It is to be appreciated that in embodiments where hydrogels are employed in the manner described above, such hydrogel-membrane structures can also be referred to as axial cores 80. The core 80 can be constructed as more fully described in U.S. Pat. No. 8,870,915, issued Oct. 28, 2014, in the name of Mayer et al. (the "Mayer Reference") and U.S. Patent Publication No. 2020/0178951 A1, published Jun. 11, 2020, in the name of Johnson et al. (the "Johnson Reference"), the entire disclosure of each of which is incorporated herein by this reference. It should be appreciated that the extent of core 80 swelling, including the radial expansion and longitudinal contraction, can be adjusted by varying certain parameters of the core 80, such as the core diameter D2, core material 84, and the type and percent by weight of the osmotically active substances 86. These parameters can be adjusted as desired to provide the suture construct 4 with advantageous size transformation in various treatment applications.

As the core 80 swells radially and contracts longitudinally, it causes the jacket 12 to also expand radially and contract longitudinally. During this size transformation, the individual fibers 90 in the jacket 12 reposition and reorient relative to each other in a manner causing the pick-count of the jacket 12 to increase.

Figure 2A:
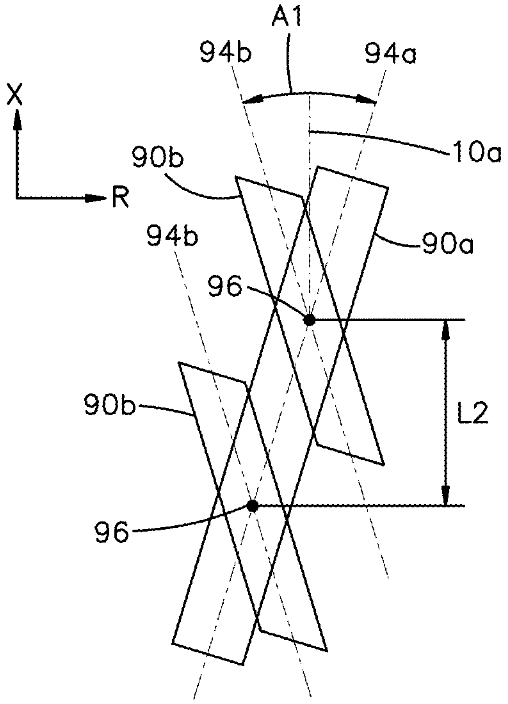
FIG. 2A is a diagram view of intersecting fibers of the suture illustrated in FIG. 1A, wherein the fibers are shown at a first configuration of the suture.
Figure 2B:
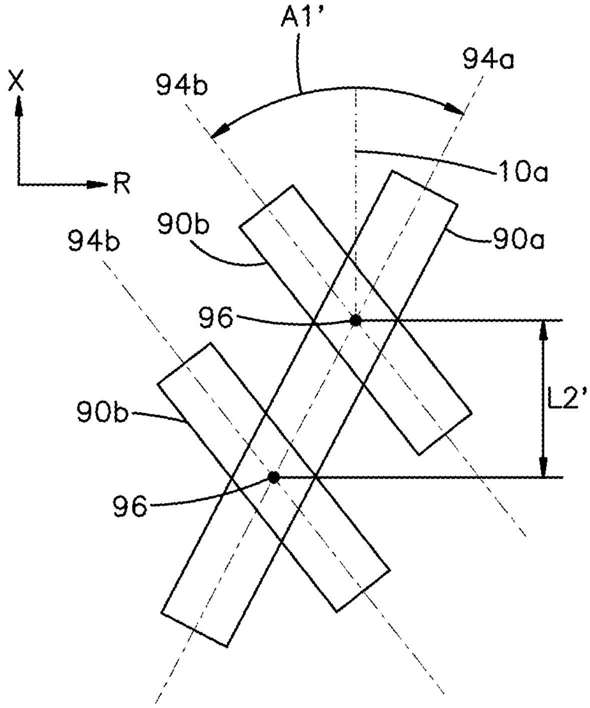
FIG. 2B is a diagram view of the intersecting fibers illustrated in FIG. 2A, wherein the fibers are shown at a second configuration of the suture.

Referring now to FIGS. 2A and 2B, a reference fiber 90*a* is shown being intersected by a pair of crossing fibers 90*b* in the first configuration (FIG. 2A) and the second configuration (FIG. 2B) of the suture 4. The reference fiber 90*a* extends along its central axis 94*a* and the crossing fibers 90*b* extend along their respective central axes 94*b*. The central axes 94*b* of the crossing fibers 90*b* intersect the central axis 94*a* of the reference fiber 90*a* at respective intersection points 96.

With reference to FIG. 2A, in the first configuration, such as a neutral configuration, such as when the suture is dry or otherwise not hydrated, the crossing fibers 90*b* cross the reference fiber 90*a* at an intersection angle A1, which can be measured as the angle that subtends between the central axes 94*a,b* of the reference fiber 90*a* and the respective crossing fiber 90*b* and crosses an axis 10*a* oriented along the longitudinal direction X. Additionally, the intersection points 96 are spaced from each other at a distance L2, such as along the longitudinal direction X in this example.

With reference to FIG. 2B, as the core 80 swells radially and contracts longitudinally during transformation to the second configuration, the intersection angle A1 increases to A1'. Additionally, the longitudinal contraction can also reduce the distance L2 between the intersection points 96 to L2'. In this manner, the radial swelling and longitudinal contraction of the core 80 actuates or "drives" reorientation of the intersection angles from A1 to A1' and can drive further repositioning of the fibers 90 (or at least some of the fibers 90), such as by reducing the longitudinal distance from L2 to L2' between adjacent crossing fibers 90*b* in the jacket 12. The inventors have observed, through testing (described in more detail below), that this reorienting and repositioning of the fibers 90 increases the average pick-count in the jacket 12.

The following embodiments employ such fiber 90 reorienting and repositioning as an actuation mechanism to further transform the suture 4 in advantageous ways. For example, embodiments that employ these changes in fiber structure for changing the surface texture of the suture 4 will be described with reference to FIGS. 3A-6C; and embodiments that employ such changes in fiber structure for providing visual feedback of a status of the suture 4 will be described with reference to FIGS. 7A-7D.

Figure 3B:
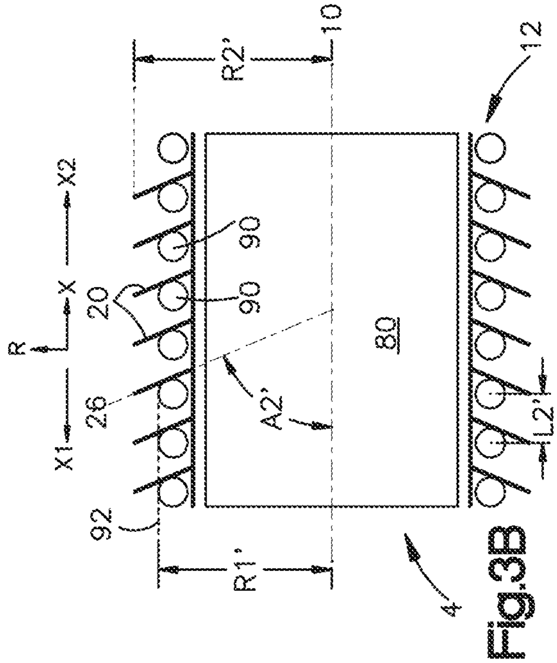
FIG. 3B is a diagrammatic, sectional side view of the suture illustrated in FIG. 3A, showing the mono-directional retention members at respective deployed orientations when the suture is in the second configuration.
Figure 3A:
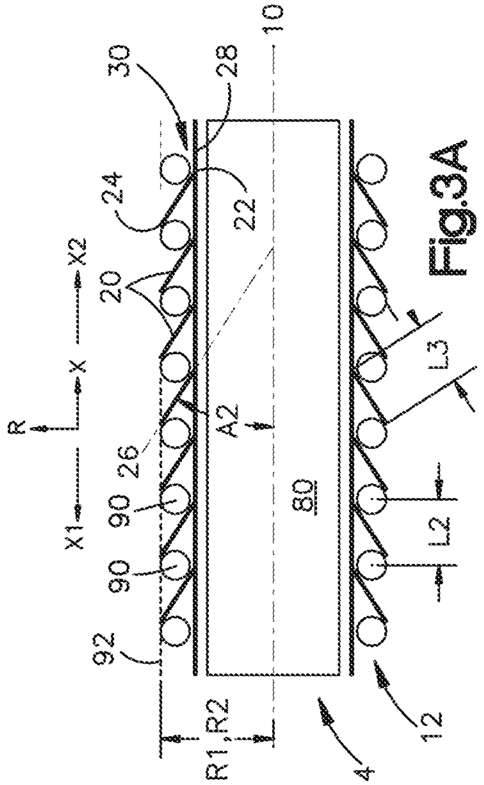
FIG. 3A is a diagrammatic, sectional side view of the suture illustrated in FIG. 1A, showing deployable, mono-directional retention members at respective orientations when the suture is in the first configuration.

Referring now to FIG. 3A-3B, the suture 4 can include a plurality of retention structures, such as barbs 20, configured to be deployed in a manner changing the surface texture of the suture 4 responsive to the size transformation. The barbs 20 can be embedded or otherwise disposed within the jacket 12 and can reside longitudinally between adjacent fibers 90. As shown, the barbs 20 can be positioned at each crossing along the longitudinal direction X. However, in other embodiment, the barbs 20 can be positioned at every other crossing, or every third crossing, or greater than every third crossing, depending on the particular retention needs for the intended treatment. The barbs 20 extend from inner barb ends 22 to outer barb ends 24 along respective barb axes 26, which extend at respective barb angles A2 from the longitudinal axis 10. The barbs 20 also define a barb length L3 measured between the inner and outer ends 22, 24 along the respective barb axis 26. The barbs 20 preferably extend substantially linearly between their inner and outer ends 22, 24. However, it should be appreciated that the barbs 20 can have various other geometries, including curved, hooked, zig-zag, and the like. The inner ends 26 of the barbs 20 can be carried by a barb substrate 28, such as a sleeve 28, which can reside in an annular space 30 between the jacket 12 and the outer surface 82 of the core 80. The barb sleeve 28 is configured to provide fluid communication between the outer surface 80 of the core 80 and the aqueous environment. For example, the barb sleeve 28 can be porous or can otherwise define a plurality of openings extending radially therethrough. In such embodiments, the barb sleeve 28 can include strips of substrate material spaced apart from each other circumferentially and/or longitudinally along the length of the suture 4, such as in a net-like, mesh-like, or web-like fashion. Additionally or alternatively, the barb sleeve 28 strips can extend helically about the core 80. The barbs 20, or at least the outer ends 24 thereof, can have various material qualities, including being substantially rigid or flexible. The barbs 20 can optionally be resorbable, for example, such that as tissue healing occurs over time, the barbs 20 can be resorbed, such as if the necessity of their retention functionality diminishes over time. The barbs 20 can be constructed of a material such as polydioxanone (PDS), by way of a non-limiting example.

Referring now to FIG. 3A, the barbs 20 can be configured such that, when the suture 4 is in the first configuration, the outer barb ends 24 substantially reside within the jacket 12 or at least below the outer surface 92 of the jacket 12. Stated differently, in the first configuration, the outer barb ends 24 are preferably spaced from the longitudinal axis 10 at a radial distance R2 that is either less than or equivalent to, but not greater than, the radial distance R1 by which the outer surface 92 of the jacket 12 is spaced from the longitudinal axis 10. In such embodiments, the outer barb ends 24 preferably reside longitudinally between adjacent fibers 90 when in the first configuration. It should be appreciated that the radial distance R2 can be nominally greater than radial distance R1 when the suture 4 is in the first configuration without departing from the scope of the present disclosure.

Referring now to FIG. 3B, as the core 80 swells, it causes the jacket 12 to expand radially and contract longitudinally, reorienting and repositioning the fibers 90, as described above, including by reducing the longitudinal distance L2 between adjacent crossing fibers 90 (from L2 to L2'). As the fibers 90 move closer together and reduce distance L2, they reorient the barbs 20 by increasing the barb angles from A2 to A2', thereby forcing the outer barb ends 24 outward so that their radial distance R2' is greater than that R1' of the jacket outer surface 92. As the barbs 20 are driven or "deployed" outward responsive to the suture transformation, the barb angles A2' can be referred to as "deployed angles" A2'. In the second configuration, such as when the barbs 20 are fully deployed, the deployed barb angles A2' can be up to about 10 degrees greater than the barb angles A2 at the neutral configuration. It should be appreciated that, because the jacket 12 is constructed of intertwined fibers 90, preferably according to a textile fabrication process, such as braiding, knitting, weaving, winding, and the like, there can be slight variances in the foregoing dimensions R1, R1', R2, R2', L2, L2', L3, A1, A1', A2, A2' at different longitudinal locations along the suture 4 and also at different circumferential locations around the suture 4. Thus, for purposes of quantification, the foregoing dimensions R1, R1', R2, R2', L2, L2', L3, A1, A1', A2, A2' can be measured as the average of each respective dimension along the full length or a partial length of the suture 4 and along the full circumference or a partial circumference of the suture 4.

As shown in the illustrated example of FIGS. 3A and 3B, the barbs 20 can be configured such that substantially all of, or at least a majority of, the outer barb ends 24 extend away from their respective inner ends 22 along respective directions each having a directional component in only one of the first and second longitudinal directions X1, X2 (i.e., either the first longitudinal direction X1 or the second longitudinal direction X2). Stated differently, the barbs 20 can all be configured to generally face one longitudinal direction (X1 or X2). Thus, the barbs 20 of the present embodiment can be referred to as "mono-directional" barbs 20. In this manner, once deployed, the barbs 20 can provide the suture 4 with increased retention force opposing movement in the first or second longitudinal direction X1, X2 in which the barbs 20 face.

It should be appreciated that the barbs 20 can be arrayed along an entirety of the suture 4, both longitudinally and circumferentially. In other embodiments, the barbs 20 can be arrayed along less than an entirety of the suture 4, such as along one or more discrete portions of the suture 4, such as discrete longitudinal portions and/or discrete circumferential portions, while other portions of the suture 4 are devoid of barbs 20. It should be appreciated that the barbs 20 can be arrayed along various portions of the suture 4 as desired for a particular surgical procedure. It should also be appreciated that various features of the barbs 20 can be adjusted as needed, such as the barb length L3, deployed angle A3', shape, resorbability, and/or rigidity/flexibility, by way of non-limiting examples. Furthermore, any of the foregoing features of the barbs 20 can differ at various longitudinal and/or circumferential portions of the suture 4, as desired. By way of a non-limiting example, the length L3 of some barbs 20 can differ from the length L3 of other barbs 20. By way of another non-limiting example, some of the barbs 20 can be resorbable while others are non-resorbable, such that over time the resorbable barbs 20 can be resorbed while the others remain on the implanted suture construct.

Figure 4B:
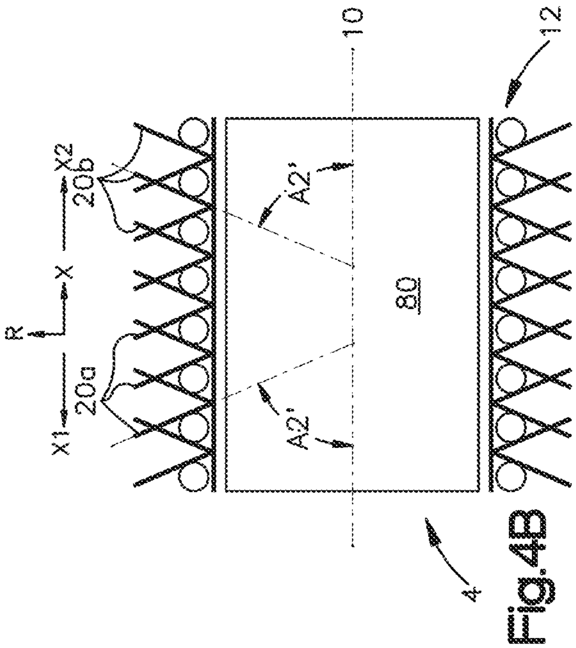
FIG. 4B is a diagrammatic, sectional side view of the suture illustrated in FIG. 4A, showing the bi-directional retention members at respective orientations when the suture is in the second configuration.
Figure 4A:
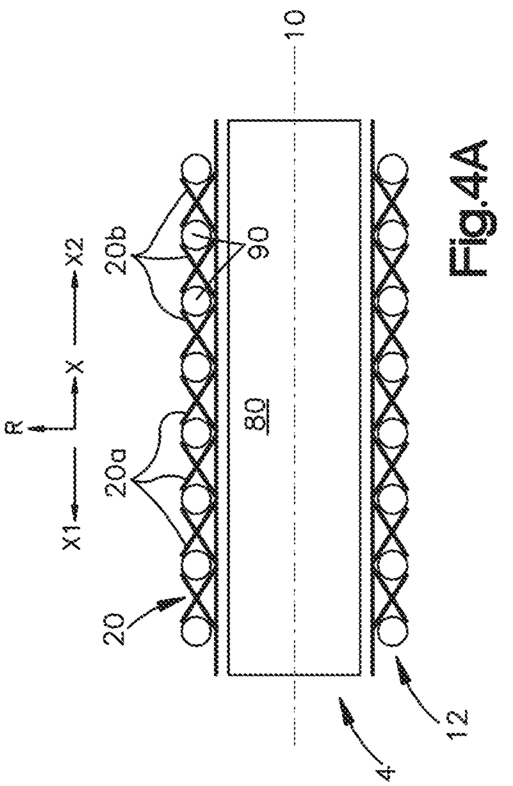
FIG. 4A is a diagrammatic, sectional side view of the suture illustrated in FIG. 1A according to another embodiment of the present disclosure, showing deployable, bi-directional retention members at respective orientations when the suture is in the first configuration.

Referring now to FIGS. 4A and 4B, in additional embodiments, the suture 4 can include bi-directional barbs 20. For example, the plurality of barbs 20 can includes a first subset 20*a* of barbs 20 that face one longitudinal direction X1, X2 (for example, the first longitudinal direction X1) and a second subset 20*b* of barbs 20 that face the opposite longitudinal direction X1, X2 (for example, the second longitudinal direction X2). In this manner, once deployed, the first and second subsets 20*a,b* of barbs 20 can provide the suture 4 with increased retention force opposing movement in both of the first and second longitudinal directions X1, X2. As shown, the first and second subsets 20*a,b* of barbs 20 can be interspersed with each other. In other embodiments, the first and second subsets 20*a,b* of barbs 20 can be arrayed along different discrete longitudinal and/or circumferential portions of the suture 4. For example, in some embodiments, the first subset 20*a* of barbs 20 can be located between the second end 8 and a longitudinal center of the suture 4 and can face the first longitudinal direction X1 (i.e., toward the longitudinal center), while the second subset 20*b* of barbs 20 can be located between the longitudinal center and the first end 6 of the suture 4 and can face the second longitudinal direction X2 (i.e., toward the longitudinal center). In such embodiments, once the barbs 20 are deployed, the first and second subsets 20*a,b* can resist suture 4 movement toward the longitudinal center of the suture 4. In further embodiments, the suture 4 can have one or more discrete portions having only the first subset 20*a* of barbs 20, one or more discrete portions having only the second subset 20*b* of barbs 20, one or more discrete portions having both the first and second subsets 20*a,b* of barbs 20 interspersed, one or more discrete portions that are devoid of barbs 20, and any combination of the foregoing. It should be appreciated that the barbs 20, including the first and second subsets 20*a,b*, can be arrayed along various longitudinal and/or circumferential portions of the suture 4 as desired for a particular surgical procedure.

Figure 5A:
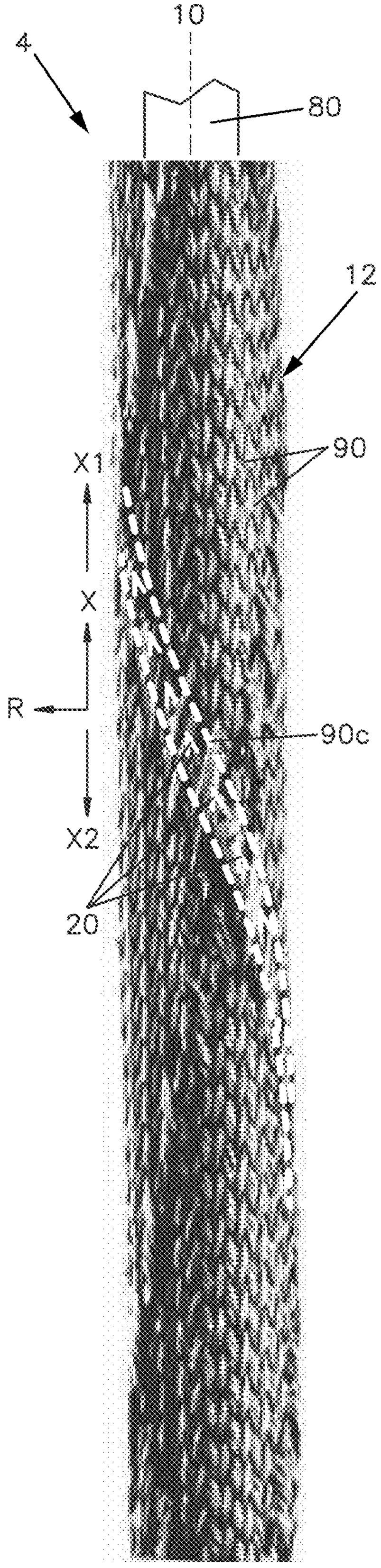
FIG. 5A is a side plan view of a suture having a helically extending fiber carrying deployable retention members, according to an embodiment of the present disclosure.
Figure 5B:
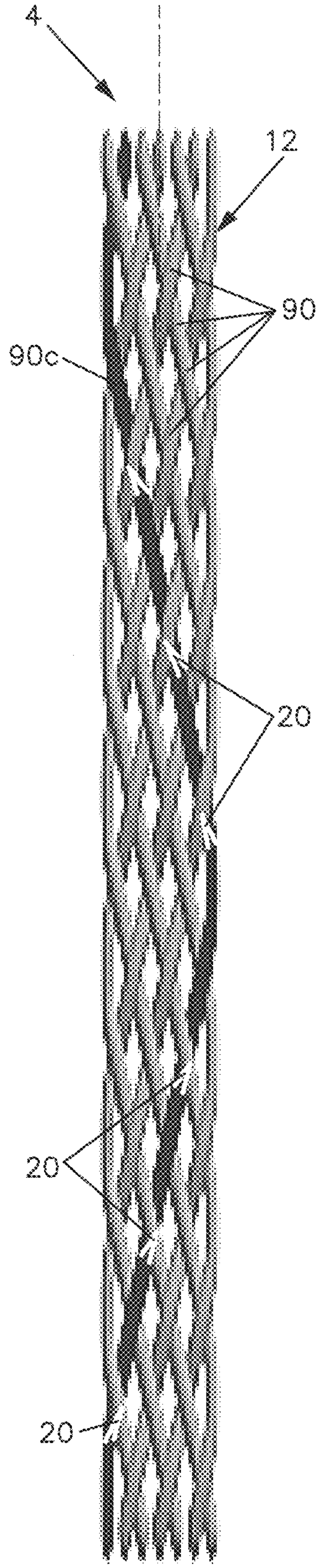
FIG. 5B is a diagram view of a braiding pattern for the suture illustrated in FIG. 5A, according to an embodiment of the present disclosure.
Figure 5C:
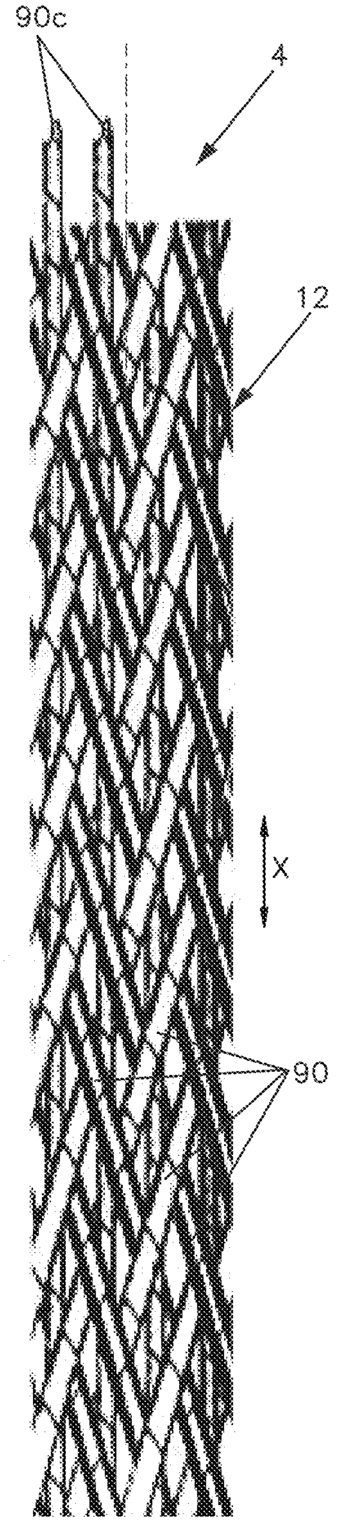
FIG. 5C is a side plan view of a suture having axially extending fibers that carry deployable retention members, according to an embodiment of the present disclosure.

Referring now to FIGS. 5A-5C, in other embodiments, the barbs 20 can be carried by one or more fibers 90*c* that are integrated (e.g., braided, knit, woven, wound, or otherwise intertwined) into the jacket 12 of the suture 4. For example, referring now to FIGS. 5A and 5B, the barbs 20 can be disposed on one or more fibers 90*c* (thus also referred to as "barb fibers" 80*c*) that are braided among other fibers 90 in the jacket 12, such as in a round braid. The one or more barb fibers 90*c* of the jacket 12 can extend helically about the core 80. The barb fibers 90*c* can be mono-filament or multi-filament fibers. According to one non-limiting example, the barb fiber 90*c* can be a mono-filament suture. The barbs 20 can be mono-directional, as shown, although each barb fiber 90*c* can carry bi-directional barbs 20. Additionally or alternatively, a bi-directionally barbed suture 4 can include at least one first barb fiber 90*c* having a plurality of mono-directional barbs 20 facing the first longitudinal direction X1 and can also include at least on second barb fiber 90*c* can carry a plurality of mono-directional barbs 20 facing the second longitudinal direction X2, by way of a non-limiting example.

Referring now to FIG. 5C, in additional embodiments, the barb fibers 90*c* can be axial fibers 90*c* that generally extend along the longitudinal direction X and are braided or otherwise intertwined with the other fibers 90 of the jacket 12. In further embodiments, the barbs 20 of the suture 4 can be disposed on a combination of one or more helically extending barb fibers 90*c* and one or more axially extending barb fibers 90*c*. In yet further embodiments, the suture 4 can be constructed such that all of the fibers 90 in the jacket 12, or at least substantially all of the fibers 90 defining the outer surface 92 thereof, can carry deployable barbs 20. In such embodiments, the barb density of each fiber 90 (i.e., the quantity of barbs 20 per inch of fiber length) can be reduced relative to the foregoing embodiments, so that the total number of barbs 20 remains the same or similar to those of the foregoing sutures 4.

It should be appreciated that the operative mechanism of deploying the barbs 20 of the embodiments described with reference to FIGS. 5A-5C is substantially similar to that described above with reference to FIGS. 3A-4B. In particular, as the suture 4 undergoes radial expansion and longitudinal contraction, the fibers 90, 90*c* reorient and reposition relative to each other, pushing the outer ends 24 of the barbs 20 radially outward from the outer surface 92 of the jacket 12.

Referring now to FIGS. 6A-6D, in other embodiments, a suture construct 50 with deployable barbs 20 can have a substantially flat, tape-like geometry, and can thus be referred to as a "suture tape" or simply a "tape" 50. In such embodiments, the tape 50 can be fabricated from a flat braid of suture fibers 90 that are braided or otherwise intertwined in a manner allowing the constructed tape 50 to lie substantially flat. The tape 50 can define a length L4 measured along the longitudinal direction X and a width W measured along a lateral direction Y that is substantially perpendicular to the longitudinal direction X. The tape 50 can also define a thickness t measured along a transverse direction T that is substantially perpendicular to the longitudinal and lateral directions X, Y. When the tape 50 is in the planar configuration, the length L4 is preferably greater than the width W, and the width W is preferably greater than the thickness t. For instance, the width W can be several times greater than the thickness t. In such embodiments, the tape 50 can be characterized as having a flat, substantially planar structure. It should be appreciated that, when the thickness t of the tape 50 is nominal in relation to the length L4 and width W thereof, the tape 50 can be referred to as a "two-dimensional" suture construct. It should also be appreciated that the tape 50 can be folded or otherwise manipulated as necessary, such as to form a "three-dimensional" anchor construct, by way of a non-limiting example. The tape 50 includes a first end 51 and a second end 52 longitudinally spaced from each other so as to define the length L4. The tape 50 also extends from a first lateral edge 53 and a second lateral edge 54 spaced from each other along the lateral direction Y so as to define the width W. The tape 65 also has a first side 57 and a second side 58 (which in the present embodiment are generally flat when the tape 50 is in the planar configuration) spaced from each other along the transverse direction T so as to define the thickness t. In some embodiments, the tape 50 can include a flat, two-dimensional portion adjacent one or more one-dimensional portions. For example, the tape 50 can include a flat portion (e.g., constructed from a flat braid) having two one-dimensional portions (e.g., constructed from round braids) extending longitudinally from the opposite ends 51, 52 thereof, such that the tape 50 has a “round-flat-round” braided construction.

The tape 50 is configured to undergo a size transformation when hydrated. For example, the tape 50 can swell along the transverse direction T. To achieve this, the tape 50 can include a braided, woven, knit, or wound structure of fibers 90 that surround a material that provides the swelling functionality, such as at least one core structure 80, which can be configured as described above. The least one core structure 80 can extend parallel with the central axis 10. In multi-core 80 embodiments, each core structure 80 defines a central core axis 85 that can extend substantially parallel with the longitudinal axis 10 of the tape 50.

Figure 6A:
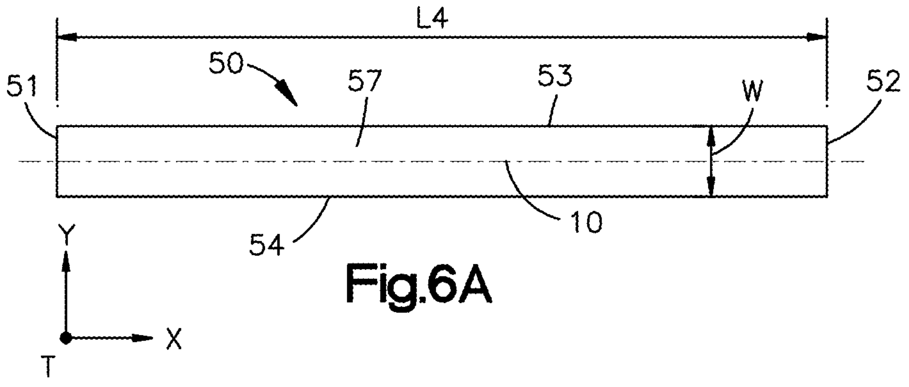
FIG. 6A is a top plan view of a suture tape constructed as a two-dimensional textile structure, according to an embodiment of the present disclosure.
Figure 6B:
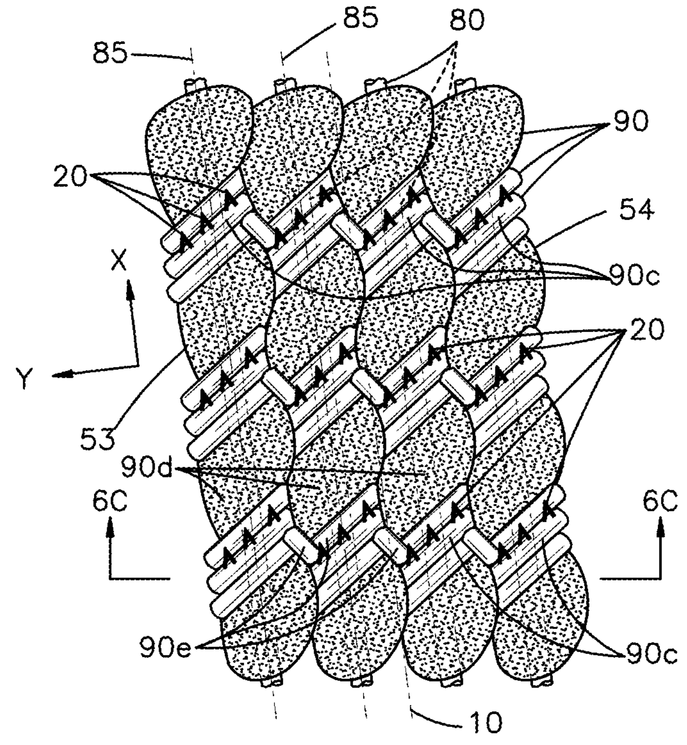
FIG. 6B is an enlarged plan view of a portion of a suture tape illustrated in FIG. 6A, according to an embodiment of the present disclosure.
Figure 6C:
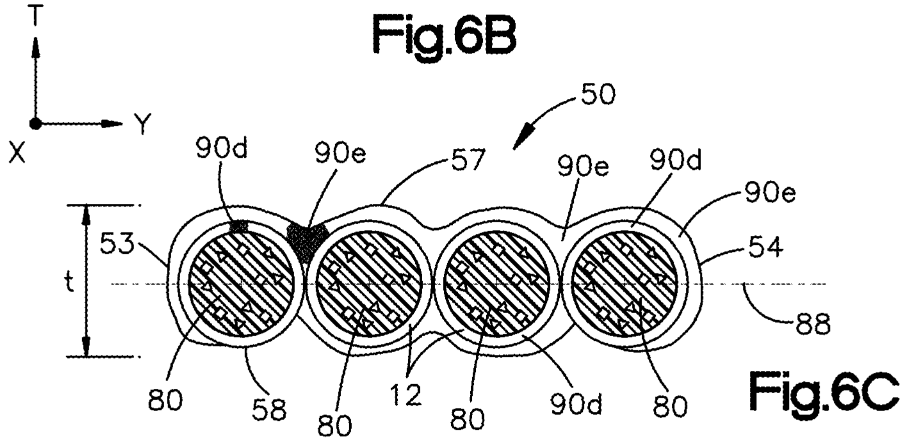
FIG. 6C is a sectional view of the suture tape taken along section line 6C-6C illustrated in FIG. 6B.

As shown in FIGS. 6B and 6C, the tape 50 can be constructed by weaving, knitting or braiding the one or more cores 80 together with a plurality of fibers 90. These fibers 90 can have a material composition as described above. The tape 50 is preferably constructed such that a first plurality of fibers 90*d* are braided in a manner so as to form a jacket 12 surrounding the core 80 (or each core 80 individually in multi-core embodiments). The first plurality of fibers 90*d* are preferably pre-braided around each of the one more cores 80. A second plurality of fibers 90*e* are then employed to interconnect the cores 80, preferably such that the cores 80 are laterally aligned with one another within the tape 50, such that each core 80 can be intersected by a single linear axis 88 that extends perpendicularly to any of the central core axes 85 and/or the central longitudinal axis 10 when the tape 50 is in the planar configuration. It is to be appreciated that the jackets 12 surrounding each core 80 are optional in this embodiment and need not be included for the tape 50 to perform advantageously.

The barbs 20 can be carried by one or more barb fibers 90*c* that are braided or otherwise intertwined together with the other fibers 90*d,e* to construct the tape 50. The mechanism for deploying the barbs 20 from the tape 50 is similar to that described above with reference to the suture 4. As the cores 80 swell radially and contract longitudinally in the aqueous environment, the thickness t of the tape 50 increases and the length L4 decreases. This causes the fibers 90*c-e* to reorient and reposition relative to each other in a manner increasing the pick-count, thereby causing the outer ends 24 of the barbs 20 to extend outward from the sides 57, 58 of the tape 50. It should be appreciated that the barb fibers 90*c* carrying the barbs 20 can be braided or otherwise intertwined within the tape 50 in various quantities and patterns to array and orient the barbs 20 as desired. Moreover, the barbs 20 can be arrayed as mono-directional or multi-directional with respect to the longitudinal direction X on one or both sides 57, 58 of the tape 50. Additionally or alternatively, the barbs 20 can also be arrayed as mono-directional or multi-directional with respect to the lateral direction Y on one or both sides 57, 58 of the tape 50. Additionally or alternatively, the barbs 20 can be arrayed along various discrete portions of one or both sides 57, 58 of the tape 50.

The suture constructs 4, 50 of the foregoing embodiments are expected to be advantageous in numerous types of treatments, particularly those involving a contact interface between the suture construct and soft tissue, such as wound closure and also more complex surgical procedures, such as rotator cuff repair. With reference to a rotator cuff repair, sutures are commonly used to anchor the damaged supraspinatus tendon to bone anchors affixed within pre-drilled holes in the greater tuberosity of the humerus. During such a rotator cuff repair using prior art sutures and techniques, surgeons commonly insert free ends of the sutures that extend from the affixed bone anchors through the damaged supraspinatus tendon and pull at least some of the free ends of the sutures to draw the lateral end of the supraspinatus tendon to the greater tuberosity of the humerus. With the sutures taut, the surgeon might tie the free ends of the sutures together, such as in pairs, at the outer surface of the supraspinatus tendon, thereby affixing the tendon to the humerus. However, the supraspinatus tendon tends to be swollen during such repairs, caused by inflammation resulting from the underlying injury and from the procedure itself. Moreover, during an arthroscopic repair, the tendon can further be swollen due to edema resulting from the use of saline to fill the joint to improve visibility during the arthroscopic repair. As the tendon heals and de-enflames post-operatively, it commonly returns to its normal, uninflamed size, which can cause laxity in the sutures connecting the tendon to the bone anchors. Such laxity can lead to micro-motion, such as repeated back-and-forth micro-translation, at the suture-tendon interface. Over time, such micro-motion can cause the sutures to progressively cut through portions of the tendon, which can negatively affect the repair.

The suture constructs 4, 50 of the foregoing embodiments can avoid or at least reduce, minimize, and/or mitigate such post-operative micro-motion across various types of suture-based repair procedures according to at least two (2) automatic mechanisms: (a) first, the longitudinal contraction of the suture 4 or tape 50 can reduce laxity as the tissue (e.g., tendon) heals and becomes uninflamed, thereby reducing micro-motion at the suture-tissue interface; (b) second, deployment of the barbs 20 can engage and grip soft tissue (e.g., tendon, muscle, ligament, cartilage) at the suture-tissue interface in a manner maintaining the relative position(s) between the suture 4 and the soft tissue, thereby further reducing micro-motion at the interface. Furthermore, these automatic mechanisms (longitudinal contraction and barb 20 deployment) preferably occur simultaneously, thereby further significantly enhancing the treatment and providing a more advantageous healing environment compared to prior art suture constructs. Even if the laxity-reducing mechanism (i.e., longitudinal contraction) occurs at less than its full extent, partial deployment of the barbs 20 can provide advantageous reduction in micro-motion at the suture-tissue interface. Similar benefits can be provided, for example, for a suture-based repair of an Achilles tendon. By way of additional examples, the suture constructs described herein, including the sutures 4 and tapes 50 described above, can be used advantageously in the various surgical repair procedures described more fully in U.S. Pat. No. 9,597,064, issued Mar. 21, 2017, in the name of Overes et al. (the “Overes I Reference”), the entire disclosure of which is incorporated herein by this reference. Moreover, those skilled in the art will recognize how the various sutures 4 described above can be employed advantageously in yet other types of surgical repairs.

Furthermore, the barbs 20 of the foregoing embodiments can be employed for increased fixation at a suture-bone interface, such as between a knot-based suture anchor and the bore of a pre-drilled hole in bone. In such surgical procedures, a tissue anchor can comprise of one or more suture constructs, such as any of the sutures 4 and tapes 50 described above. For example, the suture 4 can be employed as an actuation member that extends from a preformed knot construct, such that the suture 4 can be tensioned to cause the preformed knot construct to bunch-up into an anchoring knot. In such embodiments, the preformed knot construct can be defined by one or more additional sutures 4, tapes 50, or similar suture constructs. Additionally or alternatively, the preformed knot construct can be defined by the same suture 4 that forms the actuation member, such as by the suture 4 being woven, braided, knit, or wound in such a way to form both the preformed knot configuration and the actuation member. The deployable-barb suture constructs 4, 50 described herein can be employed in the various preformed knot configurations and repair procedures, including those that are more fully described in U.S. Pat. No. 8,828,053, issued Sep. 9, 2014, in the name of Sengun et al. (the "Sengun Reference"); U.S. Pat. No. 9,173,645, issued Nov. 3, 2015, in the name of Overes et al. (the "Overes II Reference"); U.S. Pat. No. 9,724,080, issued Aug. 8, 2017, in the name of Corrao et al. (the "Corrao Reference"); and U.S. Pat. No. 9,743,919, issued Aug. 29, 2017, in the name of Manos et al. (the "Manos Reference"), the entire disclosure of each of which is incorporated herein by this reference. The deployable barbs 20 can advantageously improve fixation at the anchor-bone interface of the foregoing embodiments and references. Furthermore, in such types of suture-based knot configurations, the deployable barbs 20 can advantageously be arrayed and configured to engage (e.g., bite into) adjacent portions of a bunched knot in a manner increasing the knot strength or otherwise prevent the knot from loosening.

In further embodiments, one or more and up to each of the barbs 20 of a suture construct 4, 50 can be configured to also be activatable to elute one or more compounds or medicaments. In such embodiments, the barbs 20, and optionally the component that carries the barbs 20 (e.g., barb substrate 28 and/or barb fiber 90*c*), can be formed of a material that is activatable to elute such compounds or medicaments. Additionally or alternatively, one or more and up to each of the barbs 20 of a suture construct 4, 50 can be configured to absorb or otherwise take up various compounds. In such embodiments, the absorption characteristics of the barbs 20 can be adjusted as needed, for example, by tailoring the specific hydrophobic/hydrophilic nature and/or surface chemistry of the polymeric barb substrate 28 and/or barb fiber 90*c* that carries the barbs 20. It should be appreciated that the barbs 20, barb substrates 28, and/or barb fibers 90*c* can be constructed from multiple materials, such as multiple polymeric materials, in a manner allowing various combinations of the foregoing features, including such features having an automatic response actuated by hydration. It should also be appreciated that the size transformation characteristics of the core 80, and thus the suture construct 4, 50, can be adapted as desired (e.g., by varying the core diameter D2 and the type and percent by weight of the osmotically active substances 86) to provide advantageous barb 20 deployment characteristics based on the needs of a specific repair application.

With reference to FIGS. 7A-8B, in additional embodiments, suture constructs, such as the sutures 4 and tapes 50 described above, can be configured such that their size transformation responsive to hydration causes a change in one or more visualization characteristics of the suture construct. Such changes in visualization characteristics (e.g., visual presentation) of the suture construct can be tailored to provide visual feedback regarding a condition of the suture construct or portions thereof. Such visual feedback can be particularly advantageous, such as when used in repairs in which the laxity-reducing features of the suture construct are superseded by the need to ascertain intra- and/or post-operative conditions of the suture construct, such as axial strain (longitudinal deformation), by way of a non-limiting example. The inventors have discovered that the pick-count of the laxity-reducing sutures 4 and tapes 50 described above (i.e., constructed with swellable cores 80) tend to be generally equivalent when in a neutral configuration (i.e., when dry and not subjected to axial loading) and when in a hydrated, axially strained configuration at certain tensile loads along the longitudinal direction X. Thus, for such types of repair procedures, a suture construct 4, 50 can include visual indicia on the outer surfaces thereof that provide visual indication(s) (i.e., visual feedback) of longitudinal strain experienced by the suture construct 4, 50.

Figure 7B:
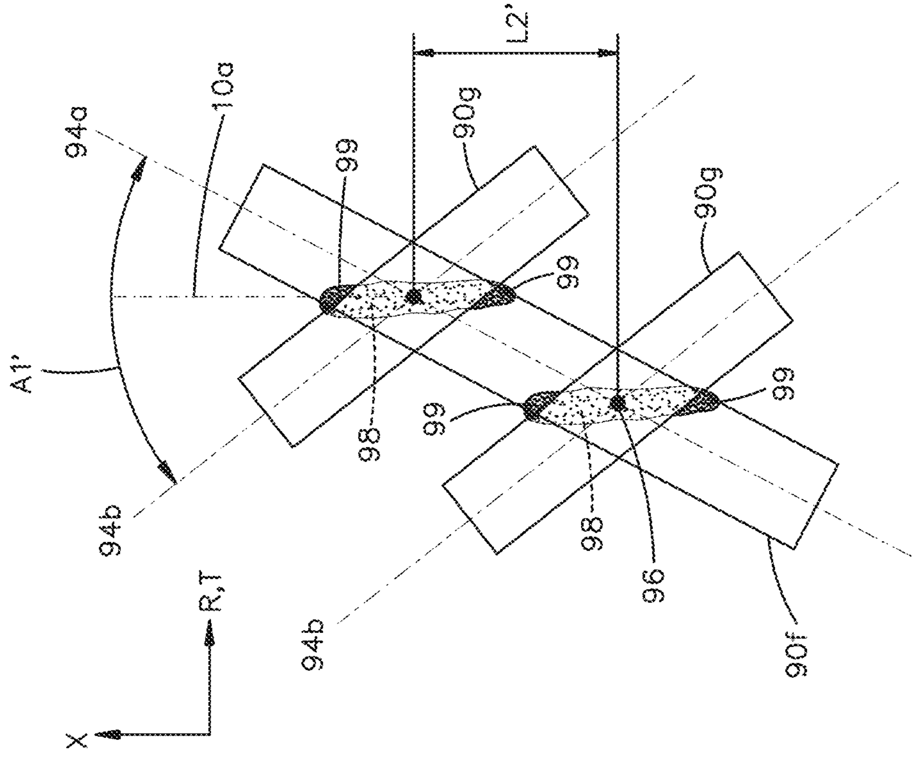
FIG. 7B is a diagram view of the intersecting fibers illustrated in FIG. 7A, wherein the fibers are shown at a second visual configuration of the suture construct.
Figure 7A:
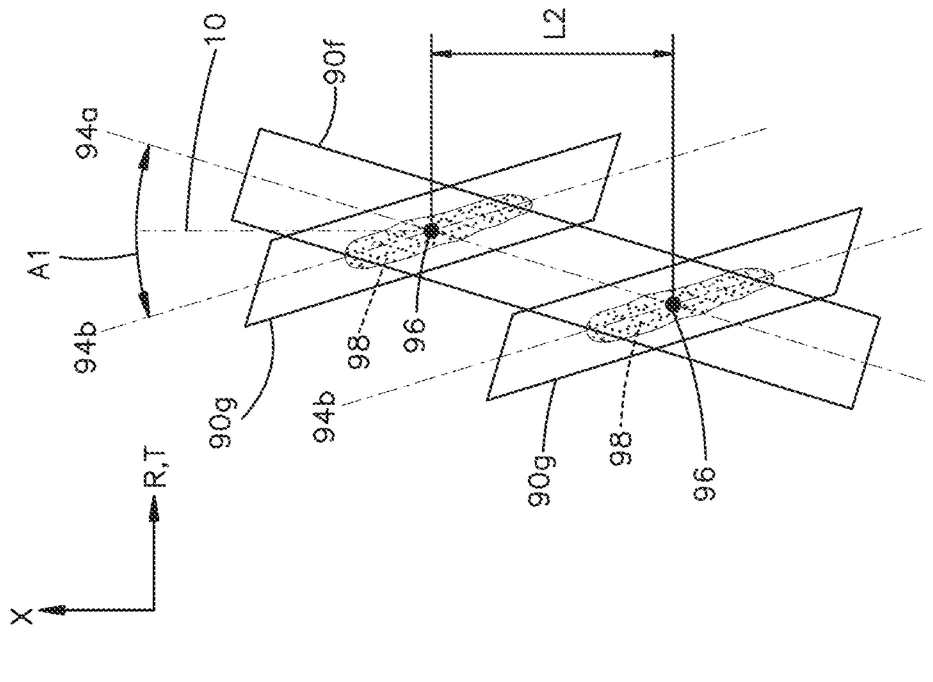
FIG. 7A is a diagram view of intersecting fibers of a suture construct, wherein the fibers are shown at a first visual configuration of the suture construct, according to an embodiment of the present disclosure.

In such embodiments, some and up to all of the fibers 90 at the outer surface of a suture construct 4, 50 can have discrete visual indicia presented thereon. For example, as shown in FIGS. 7A and 7B, the visual indicia can include colored tracer filaments located at discrete portions 98 of a first subset 90*f* of fibers 90. These discrete portions 98 can be referred to as "tracers" 98. As shown in FIG. 7A, the tracers 98 can be located at regular intervals along the axis 94*a* of the first subset 90*f* of fibers 90, such as at intersection locations 96 at which outer surfaces of the first subset 90*f* of fibers 90 are crossed by a second subset 90*g* of fibers 90 when the suture construct 4, 50 is in a first visual configuration, such as when the suture construct 4, 50 is hydrated and at a first, preferred axial load or preferred range of axial load. If the suture construct 4, 50 or a portion thereof subsequently experiences a reduction in longitudinal tensile force (such as resulting from a size reduction in repaired anatomy, e.g. reduced inflammation, or resulting from a position shift in repaired anatomy), the core(s) 80 can drive longitudinal contraction of the suture construct 4, 50 or portion thereof.

Referring now to FIG. 7B, as described above, such longitudinal contraction increases the pick-count and preferably increases the intersection angles A1 between the fibers of the first and second subsets 90*f,g* from A1 to A1', which can expose or otherwise uncover or unobscure portions of the colored tracers 98, such as end portions 99 thereof. As this change replicates across a multiplicity of the intersecting fibers 90*f,g* of the suture construct 4, 50 (or portions thereof) responsive to the strain change, the resulting change in overall visual presentation can manifest as a pattern change and/or coloration change across such portions of the suture construct 4, 50 undergoing the strain change. Additionally or alternatively, the colored tracers 98 can be configured so that at least portions thereof become exposed as the distances L2 between fiber intersection points 96 are reduced from L2 to L2'.

Figure 8A:
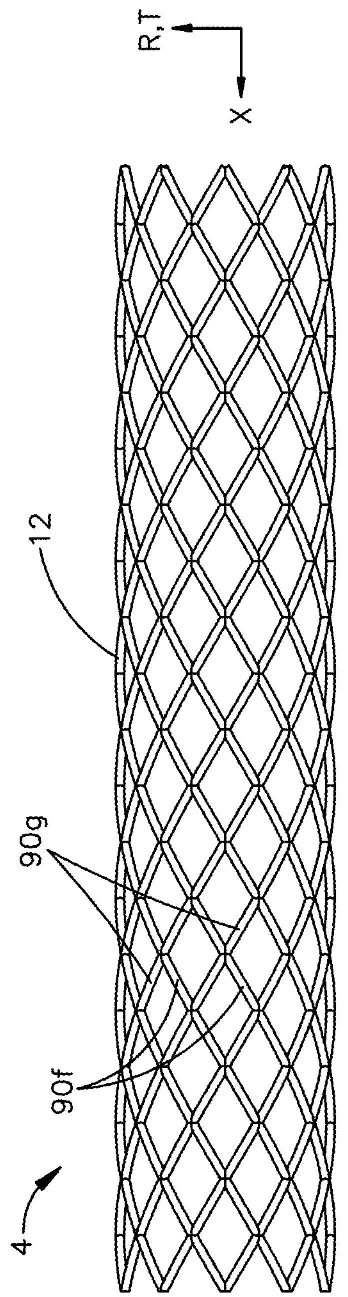
FIG. 8A is a side plan view of a portion of a suture in the first visual configuration, according to an embodiment of the present disclosure.
Figure 8B:
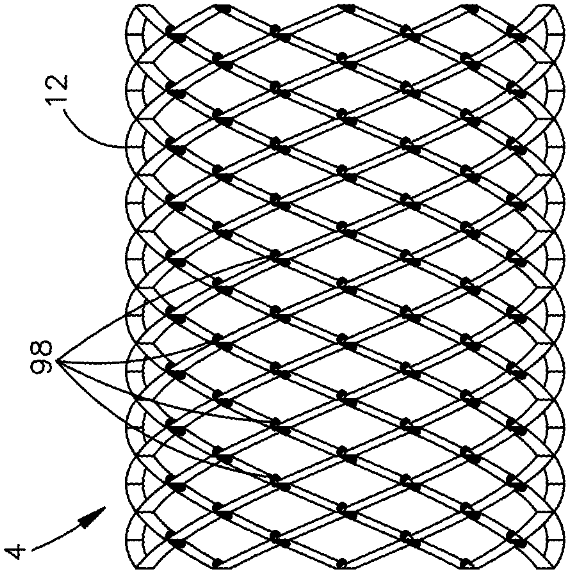
FIG. 8B is a side plan view of the portion of the suture illustrated in FIG. 8A in the second visual configuration, according to an embodiment of the present disclosure.
Figure 9A:
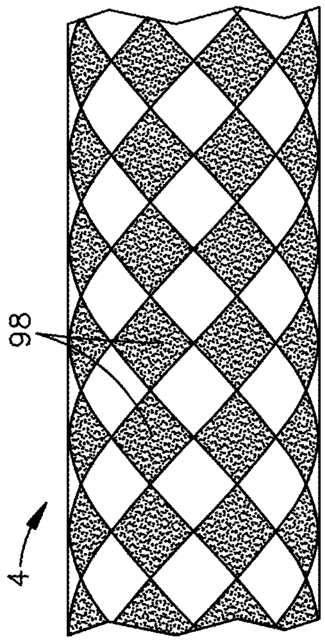
FIG. 9A is a side plan view of a portion of a suture according to another embodiment of the present disclosure in a first visual configuration.
Figure 9B:
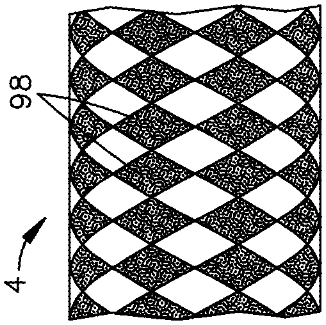
FIG. 9B is a side plan view of the portion of the suture illustrated in FIG. 9A in the second visual configuration.

Referring now to FIGS. 8A and 8B, according to one non-limiting example, a suture construct 4, 50, can be configured such that, when in the first visual configuration (e.g., in which the suture construct 4, 50 is at a preferred strain condition), substantially all of the colored tracers are covered or otherwise obscured by the second plurality of fibers 90*g*. In such embodiments, any colored tracers 98 or portions thereof that become visible can indicate an unintended change in strain (e.g., departing from the preferred strain condition) along the respective portion of the suture construct 4, 50. In other embodiments, the suture construct 4, 50 can be configured such that, when in the first visual configuration, the colored tracers 98 or portions thereof are exposed so as to present a visible pattern or design. Then, should the suture construct 4, 50 or portions thereof undergo a change in strain away from the preferred strain condition, the colored tracers 98 or portions thereof along such portion of the suture construct 4, 50 become covered, obscured, or otherwise non-visible along portions of the. In yet other embodiments, the suture construct 4, 50 can be configured such that, when in the first visual configuration, the exposed colored tracers 98 or portions thereof present a first visible pattern or design, which then changes to one or more different visible patterns or designs along respective portion(s) of the suture construct 4, 50 that depart from the preferred strain condition. By way of a non-limiting example, as shown in FIGS. 9A and 9B, the first visible pattern can be a checkerboard pattern having substantially square colored regions provided by colored tracers 98 and non-colored regions, which then become compressed and non-square (e.g., parallelograms) responsive to a strain change.

In other embodiments, the visual indicia can be produced by dyed, painted, or otherwise colored portions of suture fibers 90. Additionally or alternatively, visual indicia can be produced by removing color from, or changing the color of, colored suture fibers 90, such as by bleaching and the like. In additional embodiments, the visual indicia can include radio-opaque members incorporated into and/or among the fibers 90. For example, the suture construct can include one or more tracer threads or fibers 90 that are radio-opaque or have discrete radio-opaque portions that cause the suture construct or portions thereof to present a change in visual presentation (e.g., pattern, design), as viewed under X-ray and/or fluoroscopic imagery, responsive to a strain change. In additional embodiments, the visual indicia can include ultrasonically observable members incorporated into and/or among the fibers 90. For example, the suture construct can include one or more tracer threads or fibers 90 that are ultrasonically observable or have discrete ultrasonically observable portions that cause the suture construct or portions thereof to present a change in visual presentation (e.g., pattern, design), as viewed in ultrasound imagery, responsive to a strain change. In further embodiments, the visual indicia can include a change in visible surface texture on the outer surface of the suture construct, such as by presenting bumps or protrusions at one configuration, such as at a low strain, that changes to a smooth surface texture at another configuration, such as at high strain, and vice versa. Such changes in surfaces texture can provide the physician with additional visual clues as to the strain state of the suture construct.

In yet other embodiments, the suture constructs 4, 50 can be configured such that the automatic size change and pick-count change responsive to hydration can cause one or more fibers 90 to fracture, thereby exposing fractured portions, such as broken ends, of the fibers 90. The fractured portions of the fibers 90 can be a different color than the non-fractured portions of the fibers 90. In this manner, the presence of fractured portions of the fibers 90 can cause the suture construct to change in visual presentation. Additionally or alternatively, the fractured portions of the fibers 90 can release a dye to provide a change in visual presentation. Additionally or alternatively, the fractured portions of the fibers 90 can release a medicament. It should be appreciated that these embodiment that employ broken portions of the fibers 90 to cause a change in visual presentation can be used for providing visual feedback indicating that a portion of the suture construct has experienced mechanical failure and can thus involve a one-time occurrence signaling that the suture construct is in need of replacement. It should be appreciated that the size transformation characteristics of the core 80, and thus the suture construct 4, 50, can be adapted as desired (e.g., by varying the core diameter D2 and the type and percent by weight of the osmotically active substances 86) to provide advantageous changes in the visual presentation of the suture construct 4, 50 based on the specific needs of a repair application.

It should be appreciated that, in further embodiments, a suture construct 4, 50 can be configured to undergo a change in both surface texture (e.g., via deployable barbs 20) and visual presentation (e.g., exposure/obscuration of colored tracers 98) responsive to hydration.

It should also be appreciated that any of the embodiments disclosed above (e.g., having deployable barbs 20 and/or changing visual presentation) can be employed in various three-dimensional suture constructs, such as sutures 4 and/or tapes 50 that are folded, bent, tied, or otherwise shaped and/or combined into larger suture constructs. By way of one non-limiting example, the embodiments disclosed above can be incorporated into a mesh constructed from a plurality of sutures 4 that are braided, knit, woven, wound, or otherwise intertwined together.

The change in pick-count for the suture constructs described above was discovered following a series of tests the inventors performed to determine whether exposing sutures and their cores, similar to the sutures 4 described above, to hydration resulted in a change in pick-count. Three (3) samples of suture, particularly three (3) braid samples of Size 2 DYNACORD™ (5.0 mm diameter D1), were tested. These samples were: (1) Part No. 114290, Lot No. PRD027201, blue-colored, non-sterile suture, bulk packaged from braider; (2) Part No. 114291, Lot No. L990490, white-blue-green-colored, sterile suture, sample taken from engineering build 103333333; and (3) Part No. 114292, Lot No. PRD027564, white-black, non-sterile suture, bulk packaged from braider. Each suture was placed in a respective 250 ml sample cup that was filled with saline solution having 0.9% saline and the cup was enclosed with a lid. The cups were then put into a temperature controlled chamber at 37.1° C. (about 98.8° F.) for approximately 21 hours. The sutures were then removed from the saline and their pick-counts measured using a SmartScope optical imaging device according to pick-count test method TM-101953. To limit the amount of suture handling during inspection, the sutures were placed directly on the SmartScope glass and measured at two (2) locations per suture. The results of these tests are listed below in Table 1:

TABLE 1

| Sample | Measurement 1 (picks per inch) | Measurement 2 (picks per inch) |
|---|---|---|
| 1- Dry | 71 | 71 |
| 1- Hydrated 1 | 76 | 76 |
| 1- Hydrated 2 | 76 | 77 |
| 1- Hydrated 3 | 76 | 76 |
| 2- Dry | 70 | 71 |
| 2- Hydrated 1 | 76 | 76 |
| 2- Hydrated 2 | 76 | 76 |
| 2- Hydrated 3 | 76 | 77 |
| 3- Dry | 71 | 71 |
| 3- Hydrated 1 | 76 | 76 |
| 3- Hydrated 2 | 76 | 76 |
| 3- Hydrated 3 | 75 | 76 |

These results demonstrate that a hydration time of about 21 hours at body temperature increased the pick-count for these sample sutures by about 5 pick (also measured as 5 ppi (picks-per-inch)). From these tests, the inventors determined that such change in pick-count resulting from the core swelling radially and contracting longitudinally could be used as an actuation mechanism to drive additional physical changes in the suture, including changes in surface texture (e.g., barb deployment) and visualization characteristics (e.g., exposing and/or obscuring colored filaments).

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A suture construct elongate along a longitudinal direction, wherein the suture construct is configured to change in size from a first configuration to a second configuration, the suture construct comprising:

an outer layer of material extending along the longitudinal direction, the outer layer of material comprising a plurality of intertwined fibers that comprises a first subset of fibers crossed by a second subset of fibers at respective intersections, wherein fibers of at least the first subset of fibers have discrete visual indicia that comprises discrete colored regions located at or adjacent the intersections, wherein the outer layer of material is configured such that the discrete visual indicia have:

a first visualization characteristic when the suture construct is in the first configuration; and a second visualization characteristic when the suture construct is in the second configuration, wherein the second visualization characteristic is visually different than the first visualization characteristic, wherein one of the first and second visualization characteristics is caused by the discrete colored regions being substantially obscured by the second subset of fibers, and the other of the first and second visualization characteristics is caused by at least portions of the discrete colored regions being substantially exposed.

2. The suture construct of claim 1, wherein the other of the first and second visualization characteristics is defined by the at least portions of the discrete colored regions collectively presenting a visible pattern.

3. The suture construct of claim 1, wherein the at least portions of the discrete colored regions include one or more end portions of the discrete colored regions that are substantially exposed when the suture construct is in the second configuration.

4. The suture construct of claim 1, wherein the discrete colored regions are defined by colored tracer filaments carried by the first subset of fibers.

5. The suture construct of claim 1, wherein the first visualization characteristic is caused by the discrete colored regions being substantially obscured by the second subset of fibers, and the second visualization characteristic is caused by the at least portions of the discrete colored regions being substantially exposed.

6. The suture construct of claim 1, wherein the discrete visual indicia comprise discrete radio-opaque regions on the first subset of fibers.

7. The suture construct of claim 1, further comprising a core elongate along the longitudinal direction, the outer layer of material extending around an outer surface of the core, wherein the core is configured to expand along a radial direction and contract along the longitudinal direction responsive to exposure to an aqueous environment in a manner causing the suture construct to transition from the first configuration to the second configuration, wherein the radial direction is substantially perpendicular to the longitudinal direction.

8. The suture construct of claim 7, wherein the outer layer of material is configured such that the core expanding radially and contracting longitudinally causes the first subset of fibers to reorient relative to the second subset of fibers in a manner at least substantially causing the discrete visual indicia to transition from the first visualization characteristic to the second visualization characteristic.

9. The suture construct of claim 7, wherein a difference between the first visualization characteristic and the second visualization characteristic indicate a change in longitudinal strain experienced by at least a portion of the suture construct.

10. A suture construct elongate along a longitudinal direction, wherein the suture construct is configured to change in size from a first configuration to a second configuration, the suture construct comprising:

an outer layer of material extending along the longitudinal direction, the outer layer of material comprising a plurality of intertwined fibers that comprises a first subset of fibers crossed by a second subset of fibers at respective intersections, wherein the first subset of fibers and the second subset of fibers are configured to reorient relative to each other in a manner causing the outer layer of material to change in one or more of surface texture and visual appearance as the suture construct changes between the first and second configurations, such that the first subset of fibers and the second subset of fibers are configured to reorient relative to each other in a manner causing the outer layer of material to change in visual appearance as the suture construct changes between the first and second configurations, wherein the change in visual appearance is caused by the reorientation of the first subset of fibers and the second subset of fibers causing discrete colored regions of the fibers to transition from an exposed state to an obscured state.

11. The suture construct of claim 10, wherein the first subset of fibers and the second subset of fibers are configured such that the reorientation of first and second subsets of fibers relative to each other also causes the outer layer of material to change in surface texture as the suture construct changes between the first and second configurations, wherein the change in surface texture is caused by the reorientation of the first subset of fibers and the second subset of fibers forcing outer ends of barbs outwardly from an outer surface of the outer layer of material.

* * * * *